(12) United States Patent
Desai et al.

(10) Patent No.: US 8,262,881 B2
(45) Date of Patent: Sep. 11, 2012

(54) METHOD FOR FINGER-PRINTING HEPARINS

(75) Inventors: Umesh R. Desai, Glen Allen, VA (US); J. Timothy King, Elliston, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 12/918,889

(22) PCT Filed: Feb. 27, 2009

(86) PCT No.: PCT/US2009/035437
§ 371 (c)(1), (2), (4) Date: Nov. 10, 2010

(87) PCT Pub. No.: WO2009/108845
PCT Pub. Date: Sep. 3, 2009

(65) Prior Publication Data
US 2011/0048946 A1    Mar. 3, 2011

(51) Int. Cl.
*G01N 27/447* (2006.01)
(52) U.S. Cl. .............................. 204/451; 514/56; 536/21
(58) Field of Classification Search .......... 204/450–455; 536/21; 514/56
See application file for complete search history.

(56) References Cited

U.S. PATENT DOCUMENTS

| 4,411,796 A | 10/1983 | Casu et al. | |
| 2008/0026375 A1 * | 1/2008 | Chen et al. | 435/6 |

OTHER PUBLICATIONS

Gunay, N.S., et al., "Capillary Electrophoritic Separation of Heparin Oligosaccharides under Conditions Amenable to Mass Spectrometric Detection", Journal of Chromatography A, 2003, vol. 1014, pp. 225-233.
Patel, R. P., et al., "A Simple Capillary Electrophoresis Method for the Rapid Separation and Determination of Intact Low Molecular Weight and Unfractionated Heparins". Journal of Pharmaceutical and Biomedical Analysis, Published Online Oct. 13, 2007, vol. 45, pp. 30-35.
Ling, A., et al., "Separation, identification, and interaction of heparin oligosaccharides with granulacyte-colony stimulating factor using capillary electrophoresis and mass spectrometry", Electrophoresis, 2005, vol. 26, pp. 3460-3467.
Timothy, K., et al., "A Capillary Electrohoretic Method for Finger-printing Low Molecular Weight Heparins". Analytical Biochemistry, Published online Jun. 4, 2008, vol. 380. pp. 229-234.

* cited by examiner

*Primary Examiner* — J. Christopher Ball
(74) *Attorney, Agent, or Firm* — Whitham, Curtis, Christofferson & Cook, P.C.

(57) ABSTRACT

Methods to generate a distinctive fingerprint (pattern of migration) for a sample of complex, polydisperse heparins are provided. The methods involve adding resolving agents such as polyamines to a heparin sample and then analyzing the sample with a technique that separates macromolecules according to charge to mass ratio (e.g. capillary electrophoresis). The resulting electropherogram is unique to and characteristic of the heparin sample. The methods may be used, for example, to monitor the quality and consistency of various heparin preparations.

15 Claims, 13 Drawing Sheets

METHOD FOR FINGER-PRINTING HEPARINS

BACKGROUND OF THE INVENTION

1. Field of the Invention

The invention generally relates to methods to "fingerprint" or resolve the migration patterns of complex, polydisperse heparin mixtures. In particular, the invention provides methods for resolving complex heparins by adding polyamine resolving agents to the mixture prior to analysis of the heparins by a technique that separates macromolecules according to charge to mass ratio.

2. Background of the Invention

Anticoagulants are molecules used to treat and prevent a number of thrombotic disorders including pulmonary embolism, deep-vein thrombosis, disseminated intravascular coagulation, acute myocardial infarction, unstable angina, cerebrovascular thrombosis, and others. Nearly 576,000 new cases of deep vein thrombosis and pulmonary embolism, two of the most common thrombotic conditions, are diagnosed every year in the US (1). Thus, a huge market exists for anticoagulants.

The two most commonly used anticoagulants are heparin (H) and low molecular weight heparin (LMWH). Heparin is a highly sulfated linear polysaccharide with an average molecular weight ($M_R$) of ~13,000 and is composed of alternating 1→4-linked uronic acid and glucosamine residues (FIG. 1). Clinically used heparin, appropriately named unfractionated heparin (UFH), is obtained from animal mucosa. UFH is a mixture of millions of chemical species differing from each other in size and chemical constitution (2,3).

LMW heparins are much smaller ($M_R$~5,000) and are produced by chemical or enzymatic depolymerization, or chromatographic separation of UFH (2). LMWHs also comprise of millions of distinct structures. In fact, they may contain additional non-native structures arising from the method of preparation.

Three LMWHs are currently approved by the Food and Drug Administration (FDA) including enoxaparin, tinzaparin, dalteparin. LMWHs are available in foreign markets such as Brazil, India, China, etc. and there is a growing discussion on the introduction of generic LMWHs in the US. LMWHs have gained market share since their introduction in 1993. The current market is approximately $4 billion per year in the US alone. Yet, they suffer from significant problems including enhanced bleeding risk, immunological reaction, patient-to-patient response variability, narrow therapeutic index, poor oral bioavailability, the need for frequent coagulation monitoring, and high cost to benefit ratio. These problems are elevated for UFH, while their frequency is reduced somewhat with LMWH.

The many adverse side effects of heparin and LMWH arise from their structure. The presence of large numbers of sulfate and carboxylate groups makes these polymers the strongest acid in human physiology. This acidity induces interaction with practically any protein that carries a cationic domain (4). A conservative estimate puts the number of heparin-binding proteins in the human body at more than 100. Yet, these interactions are different and unpredictable for different heparin or LMWH chains because their microscopic structures are different. These differences are perhaps the single major source of complications associated with heparin therapy. This structural heterogeneity has led the FDA to recommend that each LMWH should be considered as an independent drug with its own anticoagulant profile (5,6). Thus, patients on enoxaparin may not be routinely switched to tinzaparin and vice versa.

The differences in the structural and clinical profiles of LMWH have led to a large number of biophysical studies on developing methods for identifying these differences. Of particular interest is the ability to reliably assess product identity and quality in a routine manner, especially in view of the large number of sources of heparin and heparin-derived products that are available for medical use. Polyacrylamide gel electrophoresis in combination with cationic dye color development has been used to analyze heparin polydispersity (7-11). Likewise, size exclusion/gel permeation chromatography has been used to assess the average molecular weight and/or oligomeric composition of heparin (8,11-19). Both these techniques resolve UFH and LMWH into oligomers, especially the smaller chains, but do not provide more detailed structural information. On the other hand, chromatographic techniques, including reverse phase, ion-pairing and strong anion exchange, have been used to prepare heparin oligosaccharides as well as to perform oligosaccharide compositional analysis (20-27). More recently, a combination of liquid chromatography and mass spectrometry has been exploited to derive detailed sequence information on a variety of heparin preparations (28-33). Other techniques that have been utilized to understand UFH and LMWH structure and composition include capillary electrophoresis (CE) and nuclear magnetic resonance (NMR). NMR permits direct structure information from unmodified heparin chains and provides saccharide composition and sulfation pattern (34-37). It can also provide information on the average molecular weight of the heparin sample (18,38).

Capillary electrophoresis has been widely exploited to study UFH, LMWH and heparin oligosaccharides. The earliest application of CE to the analysis of heparins included disaccharide and oligosaccharide composition of UFH and LMWHs (39,40), which has now been modified to protocols with much better sensitivity and resolving power (41,42). Taking cue from the tandem HPLC—MS approaches to derive sequence information, a tandem CE—MS system has also been reported to perform disaccharide analysis (43). Unfortunately, these powerful systems work primarily on fragmented or smaller heparin oligomers. Analysis of unfragmented, intact LMWHs and unfractionated heparin is challenging because of the size of the biopolymers as well as its phenomenal charge. CE is a powerful technique that affords phenomenal resolution of nearly 100,000 theoretical plates, which is at least 10-fold higher than typical HPLC. CE relies on movement of charged particles and hence can be expected to be especially suited for the highly charged heparin chains. Polymeric natural and synthetic heparins have been assayed by CE techniques in low pH buffer using both the normal length (44) and short-end injection configuration (45). Typically, the main disadvantage of these polymeric species is that a wide peak is generally observed. The short end injection configuration enhanced efficiency, reduced analysis time and improved reproducibility. The analysis was highly sensitive to the pH of the buffer, but less so to the ionic strength. In an alternative approach, Toida and Linhardt have analyzed these polymers as copper complexes in an acidic buffer by reversed polarity (46), while Stefansson and Novotny have used cationic compounds to aid resolution (47). Since the introduction of CE analyses using reverse polarity (41), the trend has been to perform separations in either phosphate or formic acid buffers with pH in the range of 2 to 5. Under these acidic conditions, the Electroosmotic Force (EOF) is nearly eliminated and resolution is a direct function of the negative charge density and the structure of the analytes. Two groups have attempted to resolve LMWHs using these reverse polarity conditions with marginal results. Both Ramasamy et al. (48) and Patel et al. (49) have utilized a reverse polarity method in a bare fused silica capillary at pH 2.0-5.0 to resolve LMWH samples. Whereas the former utilized copper to detect heparin chains (240 nm), the latter utilized heparin's small absorbance at 230 nm. Yet, the resolution of LMWH samples was minimal. In fact, Patel et al. (49) observed a broad, heterogeneous peak with a width of several minutes, while Ramasamy et al. (48) reported small shoulders in the peak front portion of the electropherogram. These approaches are not useful to perform analysis of clinical LMWHs for assessing product identity and product quality. Thus, although several analytical methods are available, the prior art has thus far failed to provide an analytical method that can be implemented in routine manner to assess product identity and quality, and to authenticate the purported composition of heparin samples.

SUMMARY OF THE INVENTION

A method has been developed to accurately and consistently fingerprint unfractionated, polydisperse heparin mixtures. The method resolves broad heterogeneous heparin peaks into numerous (>20) components in a reliable, highly reproducible manner. This high level of resolution is attained by adding to the heparin sample polyamine resolving agents. When the heparin/polyamine mixture is analyzed using, for example, capillary electrophoresis (CE), the resulting electropherogram constitutes a high-resolution "fingerprint" that is characteristic of the heparin sample. Comparison of the fingerprints from two different heparin samples can reveal whether the two samples are the same or different. Thus, the method can be used, for example, to characterize heparin samples of known composition (e.g. to establish a reference or control sample), and to identify unknown samples by comparison to the reference. The method is therefore useful, for example, to monitor product quality during various stages of preparation, to monitor batch to batch variations, and to authenticate samples of which the composition or origin may be in doubt. Because the method is very fast, it is amenable to inclusion in "in-line" analyses such as those used during the preparation of heparin products, or for the consecutive analyses of large numbers of heparin samples on an industrial scale.

An exemplary embodiment of the invention provides a method of characterizing or "fingerprinting" a sample of polydisperse heparins. The method comprises the steps of 1) forming a mixture comprising said polydisperse heparins and at least one polyamine resolving agent; and 2) analyzing the mixture using a technique that separates molecules based on a charge to mass ratio, method is capillary electrophoresis. In one embodiment, the polyamine has the general structure Formula I

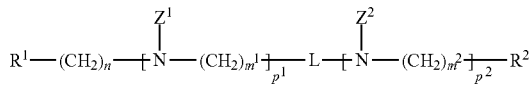

where $R^1$=NHX, where X=H or a branched or unbranched lower alkyl (e.g. C1-C3); or $R^1$ is absent; $R^2$=NHY, where Y=H or a branched or unbranched lower alkyl (e.g. C1-C3); or Y is absent; $Z^1$ and $Z^2$=H or a branched or unbranched lower alkyl (e.g. C1-C3) and may be the same or different, and $m^1$ and $m^2$=0-6 and may be the same or different; n=1-6; $p^1$ and $p^2$=0-30 and may be the same or different, but may not both be 0 (i.e. absent); and where if $p^1$ or $p^2$>1, then values of $m^1$ and $m^2$ in different p groups that are present in the polyamine may be the same or different, and $p^2$ may be absent; and L may be absent; or may be —(CH$_2$)$_q$—, where q=1-4; or may be —C(O)—(CH$_2$)r-C(O)—, where r=0-4; or may be —C(O)—C$_6$H$_4$—C(O)—. In one embodiment of the invention, L and p2 are absent, and the polyamine is selected from the group consisting of spermidine, triethylenetetramine, tetraethylenepentamine, spermine and pentaethylenehexamine. In one embodiment of the invention, L, p2, R1 and Y are absent, and the polyamine is a cyclic polyamine selected from 1,4,7-triazacyclononane and 1,4,7,10-tetraazacyclododecane. The polydisperse heparins may be, for example, low molecular weight heparins. In addition, the method may include a step of labeling the polydisperse heparins with a detectable label, e.g. a detectable organic label.

L may be, for example

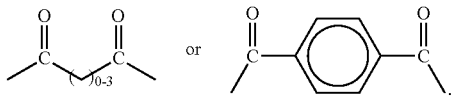

In one embodiment of the invention, the at least one polyamine has the general structure

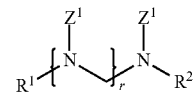

where r=1-30 and $Z^1$ may be the same or different in each instance.

In another embodiment, at least one polyamine has the general structure

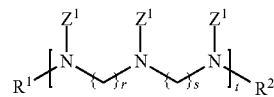

where r=1-30 and s=1-30 and t=1-30, and r, s and t may be the same or different, and $Z^1$ may be the same or different in each instance.

In yet another embodiment of the invention, at least one polyamine has the general structure

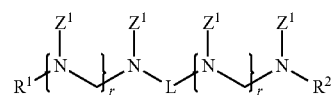

where r=1-30 and $Z^1$ may be the same or different in each instance.

And in a further embodiment, at least one polyamine has the general structure

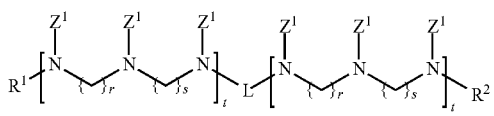

where r=1-30 and s=1-30 and t=1-30, and r, s and t may be the same or different, and $Z^1$ may be the same or different in each instance.

The invention also provides a method of verifying the authenticity of an unknown sample of complex heparins. This method includes the steps of 1) forming a mixture comprising the unknown sample of complex heparins and a resolving agent, 2) analyzing the mixture by a method that separates macromolecules according to a charge to mass ratio; then, based on results obtained in the analyzing step, 3) determining a pattern of heparin migration for the unknown sample of complex heparins; 4) comparing the pattern of heparin migration for the unknown sample to a pattern of heparin migration for a known authentic heparin sample; and, if the pattern of heparin migration for the unknown sample of complex heparins is the same as the pattern of heparin migration for the known authentic heparin sample, then 5a) concluding that the unknown sample of complex heparins is authentic. However, if the pattern of heparin migration for the unknown sample of complex heparins differs from the pattern of heparin migration for the known authentic heparin sample, then 5b) concluding that the unknown sample of complex heparins is not authentic.

The invention further provides a method for enhancing resolution, based on a charge to mass ratio, of a mixture of polydisperse heparin molecules. The method comprises the step of adding a polyamine resolving agent to the mixture of polydisperse heparin molecules prior to performing a separation of the polydisperse heparin molecules based on a charge to mass ratio.

DETAILED DESCRIPTION

The present invention provides the first demonstration of high resolution fingerprinting of mixtures of heterogeneous, polydisperse heparins. The invention utilizes polyamine resolving agents that selectively bind heparin chains to advantageously effect high resolution, reproducible fingerprinting that is characteristic of each heparin sample. When analyzed using CE, the electropherogram (fingerprint) that is obtained by the methods of the invention is characteristic of the particular heparin product or preparation and can be exploited to identify the product and to distinguish it from other heparin samples in a rapid and straightforward manner, without resorting to more complex and expensive methodology. Importantly, the method can be used to assess product quality and consistency and is thus of value to the pharmaceutical industry as well as to regulatory bodies such as the FDA. The method is also rapid and can be readily implemented in an in-line manner, e.g. during the preparation of UFH/LMWH, or for the analysis of large batches of samples from different sources.

Figure 1:
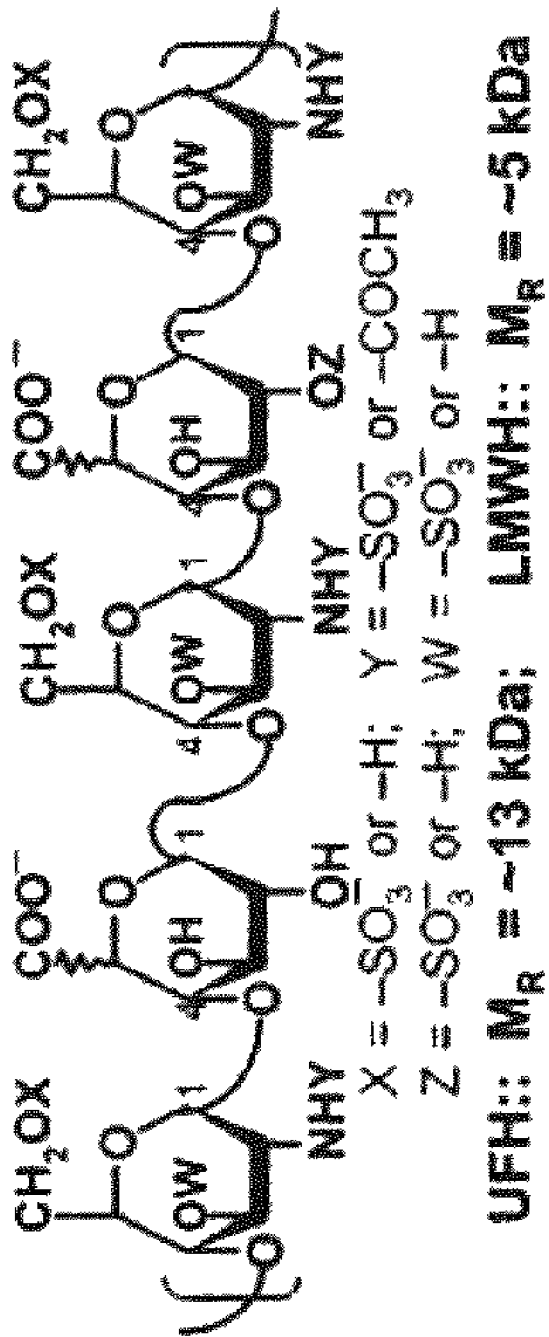
FIG. 1. Depiction of the chemical structure of a generic heparin molecule.
Figure 2:
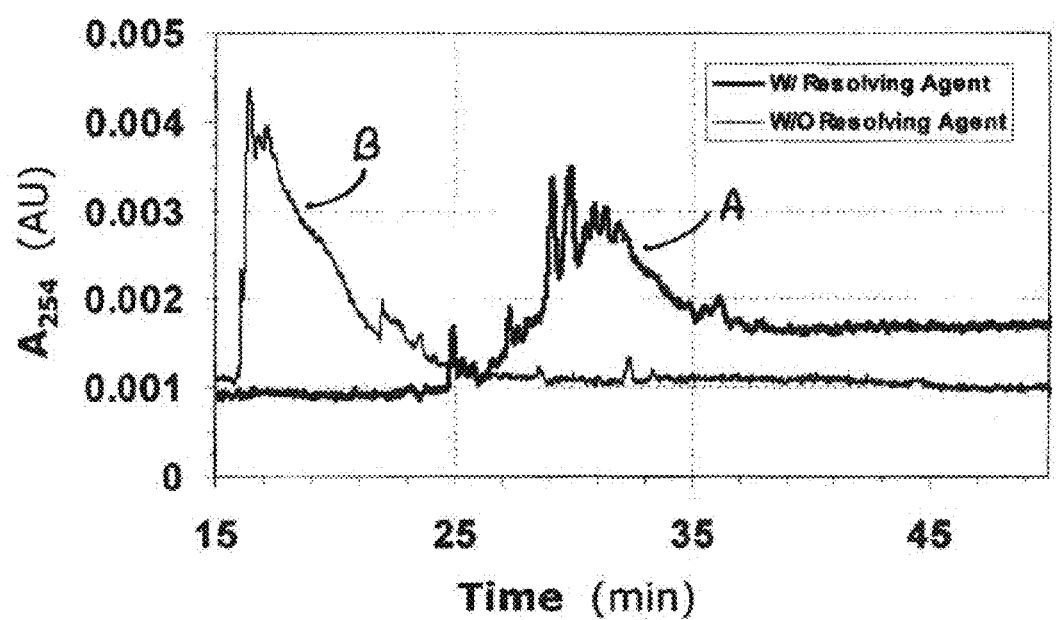
FIG. 2. Electropherogram of enoxaparin at −75 µA in 50 mM sodium phosphate buffer, pH 2.3, in the presence (trace A) and absence (trace B) of a resolving agent.

The development of this robust method for assessing heparin product identity and quality utilized the resolving power of CE. Without being bound by theory, the fundamental principle involved in the method is believed to be as follows: On application of a high negative voltage across a capillary of small diameter under strongly acidic conditions (pH 2.0 to 5.0), the highly sulfated and carboxylated polysaccharide chains migrate to the cathode (positively charged electrode). The rate of migration is dependent on the charge to mass ratio of each chain. When these chains are allowed to migrate only under the influence of the high voltage, a fairly heterogeneous broad peak is noted, implying that the charge to mass ratios of the polysaccharide chains constituting the heparin samples are not much different. However, when the chains are allowed to migrate in the presence of charge to mass ratio modifiers, referred to herein as resolving agents (RAs), the migration pattern changes dramatically. Each heparin sample yields a fingerprint electropherogram with a characteristic pattern. This fingerprint can be used to identify heparin samples such as UFH or LMWH, and can also be used, for example, to assess product consistency and quality. An exemplary fingerprint electropherogram according to the invention is presented in FIG. 2, which shows a fingerprint of enoxaparin in the presence (trace B) and absence (trace A) of a resolving agent. As can be seen, the addition of a resolving agent causes a dramatic shift in the migration pattern of the heparins in the mixture, resolving the mixture into multiple, characteristic peaks.

The resolving agents used in the practice of the invention are typically molecules containing one or more nitrogen atoms and have generic chemical structures as depicted below in Formula I:

In one embodiment of the invention, the polyamine may include an optional linker or linking moiety or group, L, as represented in Formula I.

Formula I

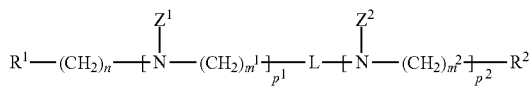

where $R^1$=NHX, where X=H or a branched or unbranched lower alkyl (e.g. C1-C3); or $R^1$ is absent;
$R^2$=NHY, where Y=H or a branched or unbranched lower alkyl (e.g. C1-C3); or Y is absent;
$Z^1$ and $Z^2$=H or a branched or unbranched lower alkyl (e.g. C1-C3) and may be the same or different;
$m^1$ and $m^2$=0-6 and may be the same or different;
n=1-6;
$p^1$ and $p^2$=0-30, and may be the same or different, but may not both be 0; and where if $p^1$ or $p^2$>1, then values of "m" in different p's that are present in the molecule may be the same or different; and
L=$-(CH_2)_q$-, where q=0-4 (i.e. if q=0, then L is absent); or
L=$-C(O)-(CH_2)r-C(O)-$, where r=0-4; or
L=$-C(O)-C_6H_4-C(O)-$.

With respect to p1 and p2, if one or both of p1 and p2>1, i.e. if multiple p1 or p2 groups are present in a polyamine molecule, then for each p group, the value of m may range from 0 to 6 independent of the value of m in any other p group. For example, if $p^1$=3, then three p groups will be present at $p^1$ in the molecule (e.g. $p_{1a}$, $p_{1b}$, and $p_{1c}$) and the value of m in each of $p_{1a}$, $p_{1b}$, and $p_{1c}$ may be the same (e.g. they are all 2); or 2 may be the same and one may differ (e.g. for $p_{1a}$ and $p_{1b}$ m is 2 but for $p_{1c}$ m is 5); or they may all differ from one another (e.g. for $p_{1a}$, m=2; for $p_{1b}$, m=3 and for $p_{1c}$ m=5).

Values of m for a plurality of p groups (e.g. $p_{1a}$, $p_{1b}$, $p_{1c}$, ... $p_{1r}$ for p1 or $p_{2a}$, $p_{2b}$, $p_{2c}$ ... $p_{2r}$ for p2) may be referred to as $m_{1a}$, $m_{1b}$, $m_{1c}$ ... $m_{1r}$ or $m_{2a}$, $m_{2b}$, $m_{2c}$ ... $m_{2r}$ etc., to correspond to the p group to which it belongs, where r is the total number of p groups in p1 or p2.

Figure 3:
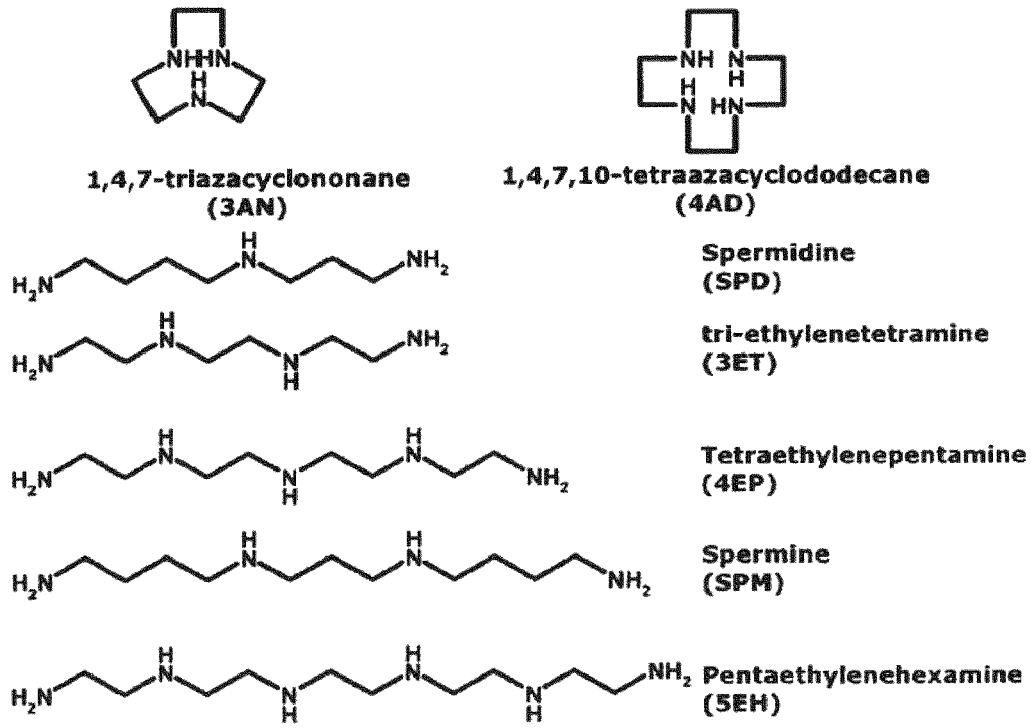
FIG. 3. Structures of exemplary resolving agents (RAs).

The polyamine RAs may be linear or non-linear (i.e. cyclic). The structures of some exemplary RAs that were found to be particularly helpful in fingerprinting heparins are shown in FIG. 3. For the compounds depicted in FIG. 3, with reference to Formula I, L is absent and p2 is absent, and:
for spermidine (SPD), n=4, $p^1$=1 and $m^1$=3;
for tri-ethylenetetramine (3ET) n=2, $p^1$=2, and for both p groups, $m^1$=2;
for tetraethylenepentamine (4EP): n=2, $p^1$=3, and for all p groups, $m^1$=2;
for spermine (SPM), n=4, $p^1$=2, and one p group $m^1$=3 and for the other $m^1$=4;
for pentaethylenehexamine (5EH): n=2; $p^1$=4, and for all four $p^1$ groups, $m^1$=2.

For cyclic polyamines, in addition to L and $p^2$, $R^1$ is also absent; Y (of $R^2$) is also absent, and the N of $R^2$ bonds directly to a terminal carbon of $(CH_2)n$. For 1,4,7-triazacyclononane (3AN), n=1 and $m^1$=2. For 1,4,7,10-tetraazacyclododecane (4AD), n=1 and $m^1$=3. Within this group of RAs, the agents that were found to be especially useful were linear polyalkylamines such as tetraethylenepentamine, spermine, and others.

An alternative representation of the polyamine when L and p2 are absent is represented by Formula II:

Formula II

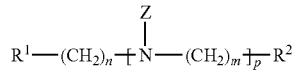

where $R^1$=NHX, where X=H or a branched or unbranched lower alkyl (e.g. C1-C3); or $R^1$ is absent (if the compound is cyclic);
$R^2$=NHY, where Y=H or a branched or unbranched lower alkyl (e.g. C1-C3); or Y is absent (if the compound is cyclic);
Z=H or a branched or unbranched lower alkyl (e.g. C1-C3);
m=0-6;
n=1-6;
p=0-30, and if $p^1$ or $p^2$>1, then values of "m" in different p's that are present in the molecule may be the same or different, as described above for Formula I.

Values of m for a plurality of p groups (e.g. $p_1$, $p_2$, $p_3$ ... $p_r$) may be referred to as $m_1$, $m_2$, $m_3$ ... $m_r$, etc., to correspond to the p group to which it belongs, where r is the total number of p groups in the molecule.

In one embodiment, the RA has the general structure

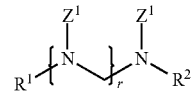

where r=1-30, and $R^1$, $R^2$ and $Z^1$ values are as described above for Formula I; and $Z^1$ may be the same or different in each instance.

In another embodiment, the RA has the general structure

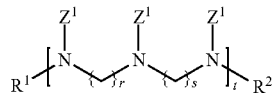

where r=1-30 and s=1-30 and t=1-30, and r, s and t may be the same or different; and $R^2$ and $Z^1$ values are as described above for Formula I; and $Z^1$ may be the same or different in each instance.

In another embodiment, the RA has the general structure

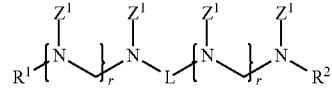

where r=1-30; and $R^1$, $R^2$, $Z^1$ and L are as described above for Formula I, and $Z^1$ may be the same or different in each instance.

In yet another embodiment, the RA has the general structure

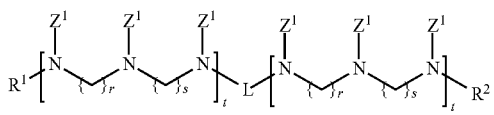

where r=1-30 and s=1-30 and t=1-30, and r, s and t may be the same or different; and $R^1$, $R^2$, $Z^1$ and L are as described above for Formula I, and $Z^1$ may be the same or different in each instance.

Figure 13:
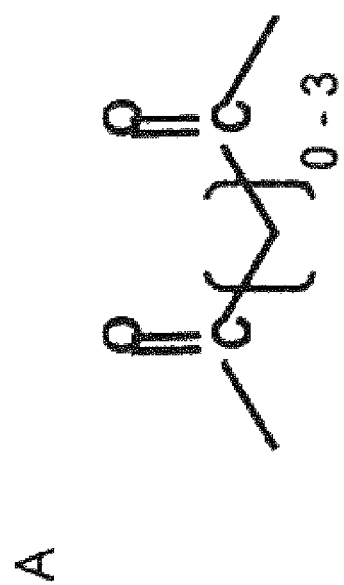
FIG. 13 depicts generic chemical structures of exemplary linking groups.
Figure 13:
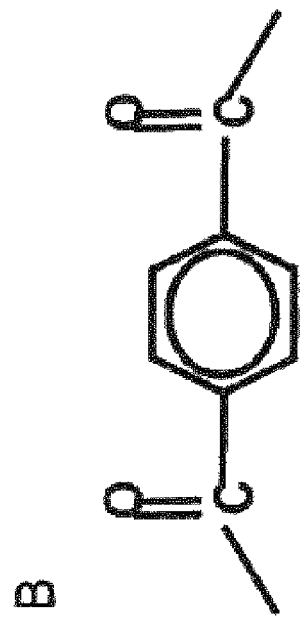

Exemplary linking groups are depicted in FIG. 13 and include

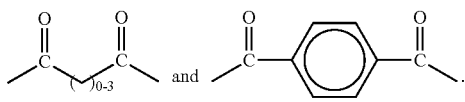

Figure 4:
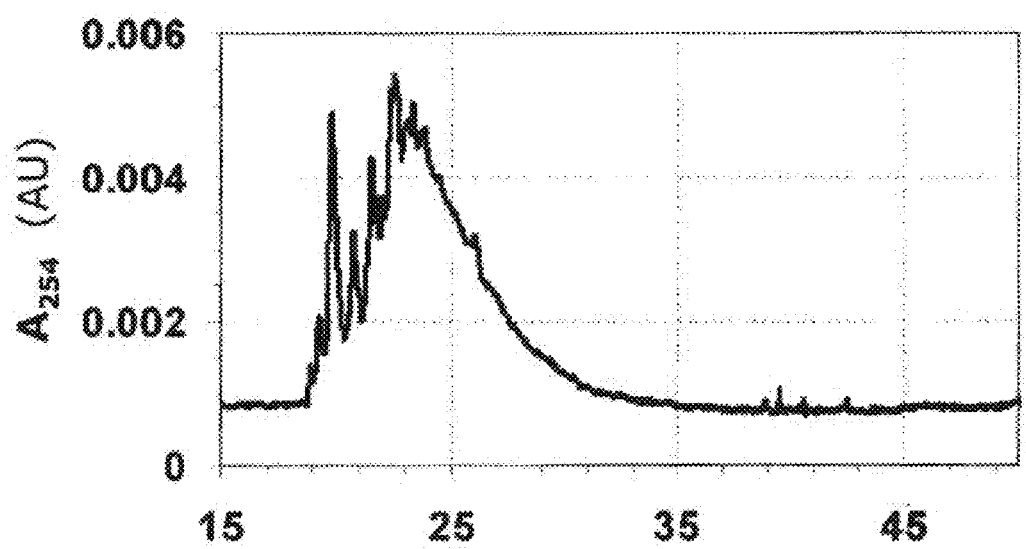
FIG. 4. Electropherogram of AMAC-labeled Lovenox® at −75 µA in 50 mM sodium phosphate buffer, pH 2.3, containing 200 spermine (SPM).
Figure 5:
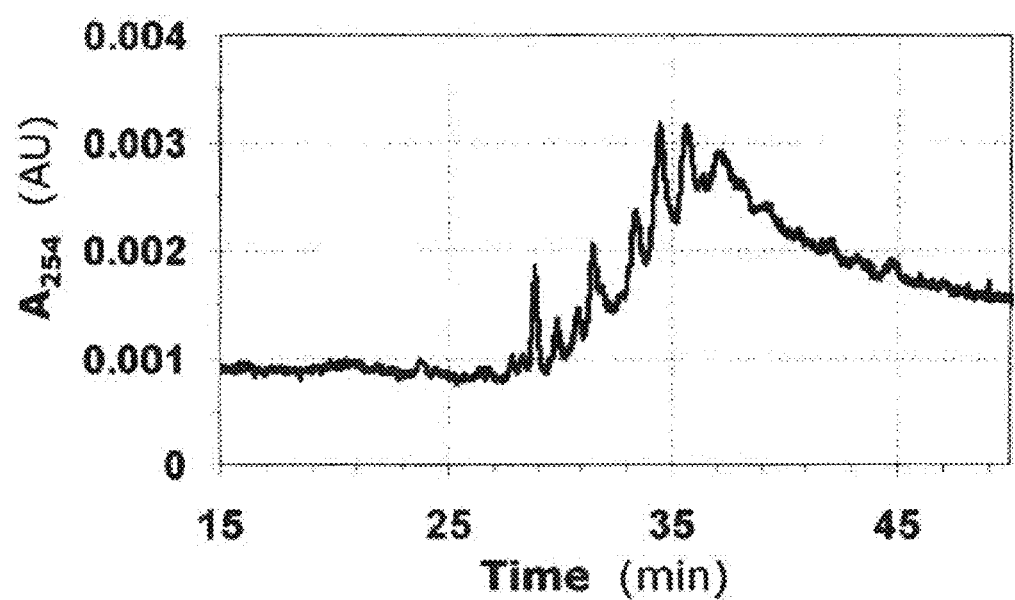
FIG. 5. Electropherogram of AMAC-labeled Innohep at −75 µA in 50 mM sodium phosphate buffer, pH 2.3, containing 200 µM spermine tetraethylenepentamine (4EP).

Additional RAs that can be used in the practice of the invention include but are not limited to
pentaethylenehexamine, hexaethyleneseptamine, septaethyleneoctamine,
octaethylenenonamine, types of RAs such as
3,6,9,12-tetra-aza-tetradecane-1,14-diamine-7,8-dione,
3,7,10,14-tetra-aza-hexadecane-1,16-diamine,
$N^1,N^4$-bis(2-(3-aminopropylamino)ethyl)teraphthalamide;
and various derivatives or modified versions of these which are known to those in the art. One or more (e.g. typically 2-3, but possibly more) of these resolving agents is combined with a heparin mixture under the conditions described herein, in order to achieve the distinguishing, high-resolution fingerprints of the invention. Mixtures of RAs may be especially useful to resolve complex mixtures of unfractionated high molecular weight heparins. FIG. 4 shows an exemplary fingerprint electropherogram of enoxaparin (Tradename: Lovenox®) at −75 μA in 50 mM sodium phosphate buffer, pH 2.3, containing 10% DMSO in the presence of 200 μM SPM as resolving agent. FIG. 5 shows an exemplary fingerprint electropherogram of tinzaparin (Tradename: Innohep) at −75 μA in 50 mM sodium phosphate buffer, pH 2.3, containing 10% DMSO, in the presence of 200 μM 4EP as the resolving agent.

The RAs are effective at different concentrations, depending in part on the composition of the heparin sample. For example, for enoxaparin, 5EH is typically useful in a 5EH concentration range of 10 to 150 μM, whereas SPM is typically useful in a concentration range of 50 to 300 μM. Within these ranges, there may be a most preferred concentration for each RA, which results in optimal resolution. For enoxaparin, the preferred concentrations of the most successful agents, 4EP, SPM and 5EH in 50 mM phosphate buffer, pH 2.3, containing 10% DMSO, are 200, 175, and 100 μM, respectively. For unfractionated heparin, a preferred concentration of 5EH is about 500 μM. Those of skill in the art, upon being apprised of the teachings herein, will be able to select, test and evaluate a particular polyamine and a particular concentration or range of concentrations for use with a particular heparin sample, and practice the method of the invention without undue experimentation.

Figure 6:
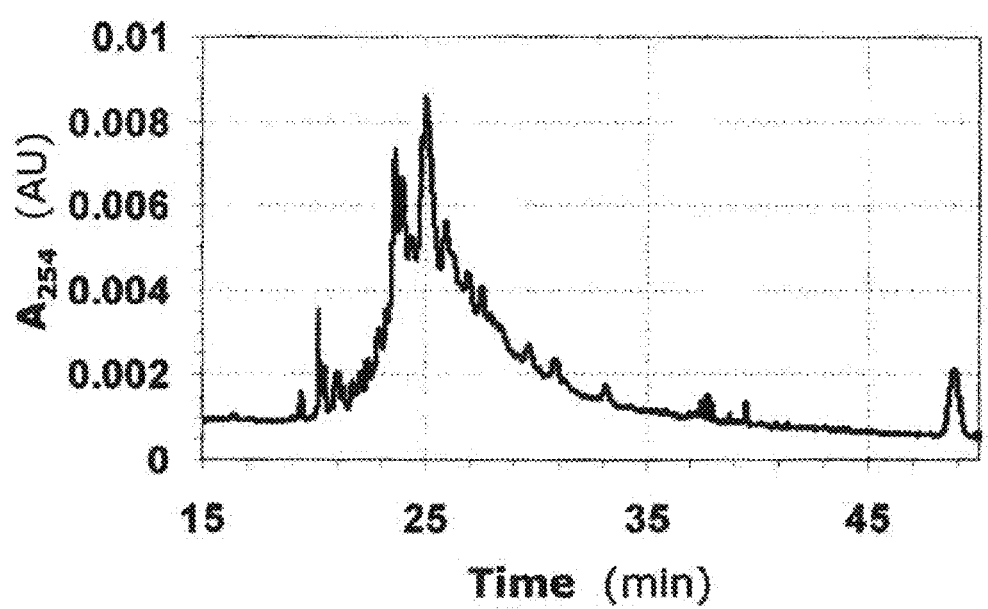
FIG. 6. Electropherogram of AMAC-labeled Lovenox® at −75 µA in 50 mM ammonium formate buffer, pH 3.5, containing 50 µM 4EP.

Fingerprinting of heparin samples can be performed with several buffers known to those of skill in the art, including but not limited to sodium phosphate, glycine-HCl, sodium acetate, sodium citrate and ammonium formate. Of these, sodium phosphate and ammonium formate are especially useful. Both of these buffers can be used within the pH range of from about 2.0 to about 5.0, although there is an optimal pH for each buffer that provides the best fingerprinting pattern. For example, pH 2.3 (FIG. 4) and pH 3.5 conditions (FIG. 6) for 50 mM sodium phosphate and 100 mM ammonium formate buffers, respectively, were found to be optimal pH conditions for resolving Lovenox®. Fingerprinting under normal polarity conditions using alkaline buffers (pH 7.0 to 9.0) was found to not resolve LMWHs effectively. Thus, fingerprinting is generally carried out under acidic conditions, e.g. at pH values below pH 7.0, or below about pH 6.0, with an exemplary pH range being from about pH 2 to about pH 5.0. The basic criteria for choosing a buffer is that it should be capable of buffering in the desired pH range. Those of skill in the art, upon being apprised of the teachings herein, will be able to select, test and determine the optimal pH or optimal pH range for use in fingerprinting a particular preparation of heparin and polyamine RA without undue experimentation.

Figure 7:
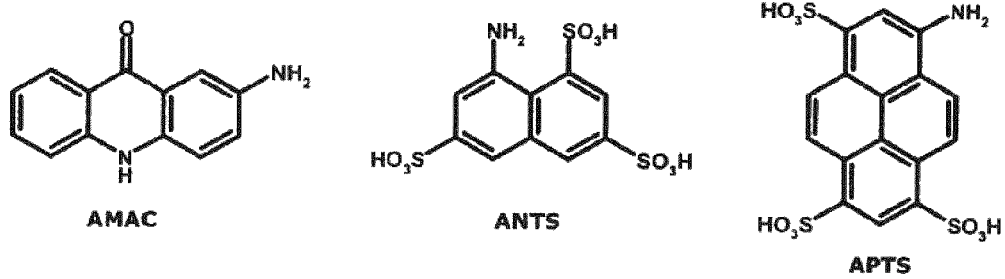
FIG. 7. Structures of chromogenic/fluorogenic UFH/LMWH organic labels (OLs).

Detection may be aided by labeling the heparin chains with chromogenic or fluorogenic organic labels (OLs) including but not limited to 2-aminoacridone (AMAC), 8-aminopyrene-1,3,6-trisulfonic acid (APTS), 2-amino-1-(4-aminophenyl)-1H-pyrrolo (2,3-b)quinoxaline-3-carbonitrile (APQC), 8-aminonaphthalene-1,3,6-trisulfonic acid (ANTS), etc. (FIG. 7). Examples of other OLs that may be used in the practice of the invention include but are not limited to 2-amino-pyridine, biotin-aminopyridine, p-aminobenzoic acid, 2-aminobenzamide, 4-aminobenzonitrile, 1-phenyl-3-methyl-5-pyrazolone (PMP), 1-(4-methoxy)phenyl-3-methyl-5-pyrazolone (PMPMP), 6-aminoquinoline, and others. The OLs are generally introduced on the reducing end of the native polysaccharide chains using reductive amination, a reaction that does not dramatically change the inherent, native structure of the polysaccharide. Each heparin sample was labeled with one of the OLs before electrophoresis. AMAC was found to be the most effective OL in terms of ease of labeling, sensitivity of detection, and stability to storage conditions. Thus, the method of the invention may also optionally include a step of labeling the heparin chains in a sample prior to analysis. In fact, in some embodiments, the heparin chains may be differentially labeled to further increase resolution, i.e. some chains or groups of chains may be labeled with one delectable label and others with a different detectable label and thus distinguished from one another. This can be accomplished by taking advantage of particular chemical groups that occur in some heparin species and not in others, or that occur with greater frequency in some species than in others. In another modification of this approach, heparin chains containing a double bond at the non-reducing end may also be utilized to fingerprint the heparin sample by monitoring absorbance at a wavelength in the range of 220-240 nm. The double bond at the non-reducing end in the heparin chains may be introduced chemically or enzymatically.

Several other parameters were found to affect resolution including the temperature of the capillary, the buffer strength, etc. However, the effects of these parameters were marginal. With respect to temperature, the analysis is generally carried out in a temperature range of from about 10° C. to about 55° C., and preferably in a range of from about 15° C. to about 25° C. With respect to buffer strength, the method is generally carried out at a buffer strength in the range of from about 10 mM to about 200 mM, and preferably in a range of from about 20 mM to about 50 mM.

In addition, the presence of excipients also can have an effect on the fingerprint that is obtained, and may be (optionally) added to increase or improve resolution, although the effect of such substances was also found to be marginal. Examples of suitable excipients include but are not limited to dimethylsulfoxide (DMSO), methanol ($CH_3OH$), ethanol ($C_2H_5OH$), N,N-dimethylformamide (DMF), and N,N-dimethylacetamide (DMA).

The methods of the invention are useful for fingerprinting any type of heparin preparation from any source. For example, unfractionated heparin from bovine, ovine, porcine sources, nitrous acid depolymerized heparin, alkali depolymerized heparin, heparinase treated heparin, chromatographically fractionated heparins, etc. Such heparins may include high, medium or low molecular weight heparins, and may be any of several known commercial preparations such asheparin sodium, enoxaparin, dalteparin, tinzaparin, fragmin, etc. In fact, a fingerprint or fingerprints for any type of heparin sample may be generated by the methods of the invention.

A single sample of heparin can display different patterns of migration, depending on which resolving agent(s) is used, and on other variables as described herein. The best or optimal fingerprint for use by an end user may vary according to several criteria, i.e. what is considered to be "optimal resolution" may differ, depending on the goals of the analysis. For example, for some purposes, it may be preferable to achieve the maximum number of peaks or maximum peak separation, whereas for other purposes, it may be preferable to sacrifice resolution somewhat in order to shorten the time of the assay. In addition, if several different, unique fingerprints are found to be equally useful, a decision to select one vs another as a standard may be made based on considerations such as e.g. the cost or availability of reagents, environmental concerns (e.g. disposal of reaction products), or other factors, etc. Those of skill in the art will recognize that such adjustments may be readily made to the variables discussed herein in order to carry out the method of the invention in a desired manner.

The preferred method of detecting the distinctive migration patterns of the invention is by using capillary electrophoresis. However, those of skill in the art will recognize that the separation of heparin mixtures may be carried out, facilitated or improved by the methods of the invention when other analytical means are employed. Examples of other techniques that may be used to separate or fingerprint heparin mixtures to which resolving agents as described herein have been added include but are not limited to reverse-phase high performance liquid chromatography, reverse-phase ion-pairing high performance liquid chromatography, etc. Basically, any method that relies on separation based on charge to mass ratios may be employed.

In some embodiments, the method of the invention is used only to provide a fingerprint or pattern of migration. In many instances, this information may be sufficient for the user (e.g. a pharmaceutical company, a regulatory body, etc.). However, those of skill in the art will recognize that the present methods can readily be incorporated into multistep or tandem analyses to provide a more complete identification of the components of a heparin mixture, if desired. For example, by using techniques such as MS, NMR, refractive index, ionic conductivity, etc., the components of peaks individually or partially resolved by the methods of the present invention can be more precisely or precisely identified. In order to do so, fractions corresponding to peaks of interest or sections of the electropherogram of interest may be collected and analyzed, with or without additional separation or purification (e.g. using additional CE, or various types of chromatography such as HPLC, gel electrophoresis, etc.). Those of skill in the art will recognize that, depending on the level of characterization or resolution required, any of many known techniques (e.g. MS, NMR, etc.) may be employed to further identify the components within a peak of the electropherogram that is produced when the method of the invention is employed, e.g. to determine the precise composition and structure of the components. Alternatively, it may be important to assess which peak contains a key heparin sequence of interest, e.g. one that has exceptional anticoagulant activity.

The method of the invention can be used for a wide variety of purposes. For example, the heparin fingerprints generated by the method can be used to identify specific products, e.g., enoxaparin, tinzaparin, and other LMWHs and/or to monitor or assess quality control. This may be particularly useful when the distributor of a heparin product does not manufacture the product in-house, but contracts manufacturing to another company. Using the methods of the invention, the distributor can easily and rapidly establish a fingerprint for use as a standard (i.e. the fingerprint of a heparin sample of known and desired composition), and thereafter monitor other purportedly similar preparations. Using the method of the invention, a user can monitor or determine the composition of the product, compared to a known standard, in order to determine product quality, lot to lot variation, compliance with manufacturing instructions, etc. In addition, regulatory institutions can use the methods for the same or similar purposes, thereby insuring product safety.

The ensuing examples are presented in order to illustrate the practice of the invention, but should not be interpreted so as to limit the invention in any way.

EXAMPLES

Example 1

Fingerprinting of Lovenox®

Three solutions were prepared. Solution A was 13.5 mg Lovenox® previously dialyzed to eliminate packaging excipients was dissolved in 260 µL of water; solution B was 25 mg of sodium cyanoborohydride in 300 µl of water; and solution C was 4 mg AMAC (FIG. 7) dissolved in 158 µL of 85% (v/v) acetic acid:DMSO. Solutions A, B and C were mixed and allowed to incubate at 37° C. for 16 hours. Following incubation, the mixture was dialyzed against high purity water to remove free, unreacted AMAC, followed by lyophilization. The solid powder so obtained was dissolved in high purity, deionized water containing 10% DMSO (v/v) at 10 mg/mL and stored at −78° C. until use.

Figure 8:
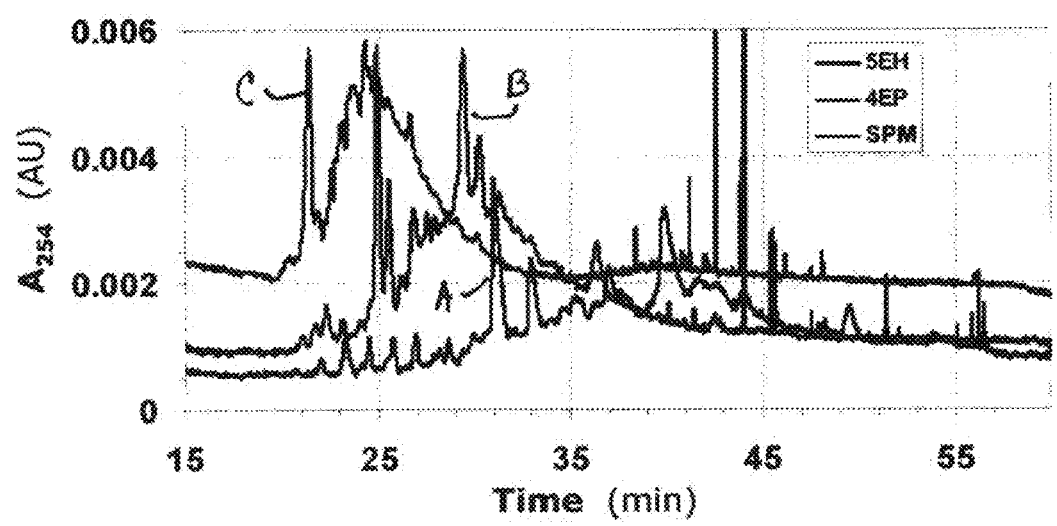
FIG. 8. Electropherogram of AMAC-labeled Lovenox® at −75 µA in 50 mM sodium phosphate buffer, pH 2.3, containing 125 µM 5EH (trace A), 4EP (trace B) and SPM (trace C).

CE was performed using a 75 µm fused silica capillary (40 cm effective length to the detector window) installed in a Beckman-Coulter P/ACE MDQ capillary electrophoresis system. A fresh capillary was activated using a 5 min flush of 1M NaOH, deionized water, 1M $H_3PO_4$, and deionized water each in sequence, while between each runs the flush time was reduced to 30 sec with a final run buffer flush of 2 mM. The stock solution of enoxaparin was diluted 10-fold with 10% DMSO/water for injection into the capillary. RA (5EH, 4EP or SPM) was added at 125 µM final concentration to the 50 mM sodium phosphate buffer, pH 2.3, containing 10% DMSO in 1 ml glass vials and loaded onto the CE buffer tray. New buffer vials were used for each run. The temperature of the capillary was maintained at 15° C. and the current was held constant at −75 µA. AMAC-labeled Lovenox® was injected for 15 seconds at 1 PSI giving a total injection amount of 150 ng. The injection volume corresponded to 7.2% of the total capillary volume. FIG. 8 shows the typical fingerprint pattern obtained for 5EH, 4EP and SPM. The electropherogram shows that the fingerprint pattern is a function of the structure of the particular RA. The fingerprint pattern is reproducible as shown below.

Example 2

Different LMWHs Display Different Fingerprint Patterns

Figure 9:
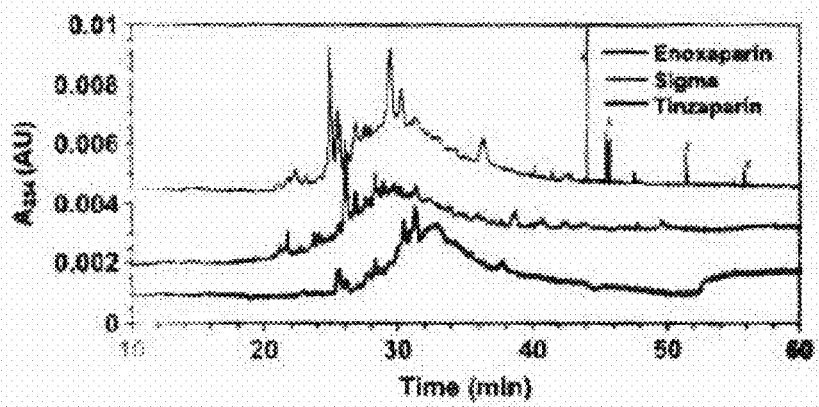
FIG. 9. Fingerprint pattern is characteristic of individual LMWHs. CE profiles of AMAC-labeled LMWHs, tinzaparin (black bold trace), enoxaparin (black thin trace), Sigma (gray bold trace), in the presence of 50 IM 4EP at −75 µA in 50 mM sodium phosphate buffer, pH 2.3, containing 10% (v/v) DMSO. Peaks marked "x" are sudden disturbances due to bubble formation during the capillary run.

To assess whether fingerprint pattern is characteristic of individual LMWHs, we compared CE runs of enoxaparin, tinzaparin, and Sigma LMWH in the presence of 50 IM 4EP at pH 2.3 (FIG. 9). As can be seen, each LMWH shows a characteristic fingerprint pattern defined primarily by the extent of interaction with the resolving agent. Whereas enoxaparin displays prominent peaks at 25 and 30 min, Sigma LMWH is devoid of the pattern at 30 min. In contrast, both these patterns are absent in tinzaparin. Also, tinzaparin displays much lower resolution than enoxaparin and Sigma LMWH. Equivalent results were observed for other resolving agents including SPM and 5EH (not shown).

Example 3

Consistency of Results Over Time

In this experiment, a generic form of LMWH from Sigma (labeled as Sigma LMWH) was used. As in Example 1, three solutions were prepared. Solution A was 35 mg Sigma LMWH (ID#H-3400), without pre-dialysis, dissolved in 500 μL of water; solution B was 63 mg of sodium cyanoborohydride in 750 μL of water; and solution C was 10 mg AMAC in 400 μL of 85% (v/v) acetic acid:DMSO. Solutions A, B, and C were mixed and allowed to incubate at 37° C. for 16 hours. Following incubation, the mixture was dialyzed and lyophilized in a manner identical to that described in Example 1. The solid powder so obtained was dissolved in high purity, deionized water to form a 10 mg/ml stock solution and stored −78° C. until use.

Figure 10:
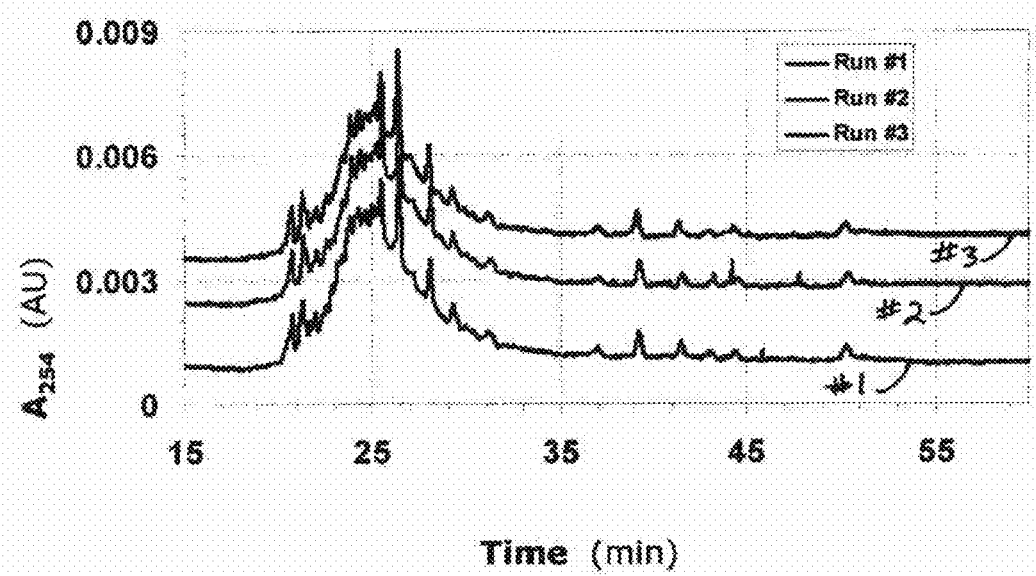
FIG. 10. Three consecutive electropherograms of AMAC-labeled Sigma LMWH at −75 µA in 50 mM sodium phosphate buffer, pH 2.3, containing 125 µM spermine (SPM).
Figure 11:
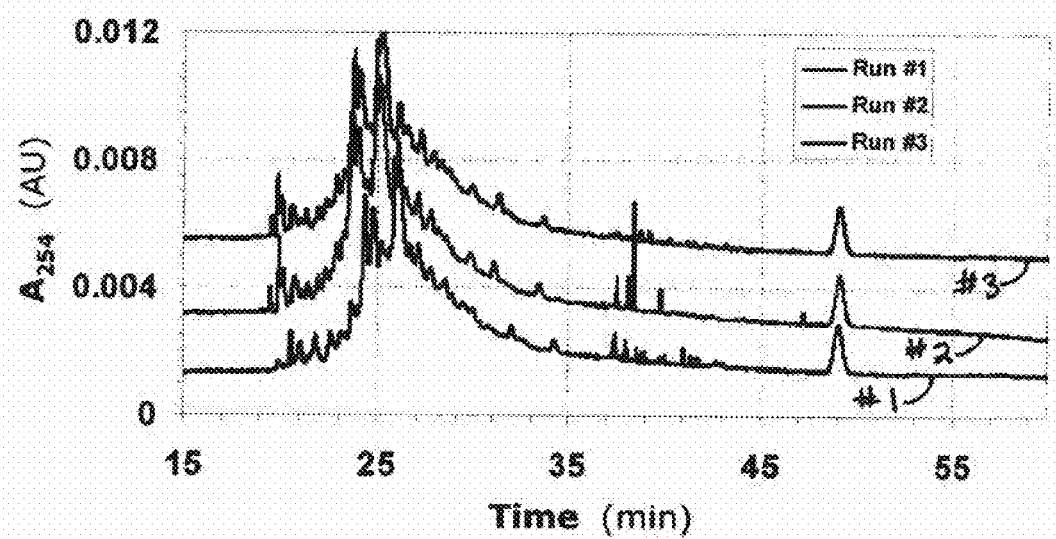
FIG. 11. Three consecutive electropherograms of AMAC-labeled Lovenox® at −75 µA in 100 mM ammonium formate buffer, pH 3.5, containing 50 µM 4EP.

Three consecutive runs were performed to assess reproducibility of the electrophoretic profile. The fingerprints are shown in FIG. 10. As can be seen, the fingerprints were highly reproducible from run to run with an intraday variation of less than 5% (FIG. 10). The variability in migration time was investigated in more detail for several resolving agents (not shown) and for AMAC-labeled Lovenox® (FIG. 11). It was observed that the protocol yields an average migration time variability of 21 s, which suggests the possibility of automated comparative analysis. With respect to interday reproducibility, a variation of approximately 5-10% in migration time and peak height was noted (not shown). The electrophoretic response displayed good linearity over a wide range concentration with a measured limit of detection and quantitation of 140±23 and 290±47 1g/mL, respectively (not shown). It is likely that the use of higher sensitivity chromo- or fluorophores or laser-induced detection may improve sensitivity. Overall, the results indicate that fingerprinting pattern, especially with multiple resolving agents, and given the stability of electropherograms, could greatly help identify and quantitate individual heparin preparations.

Example 4

Fingerprinting is Useful in Batch-to-Batch Variability Analysis

Figure 12:
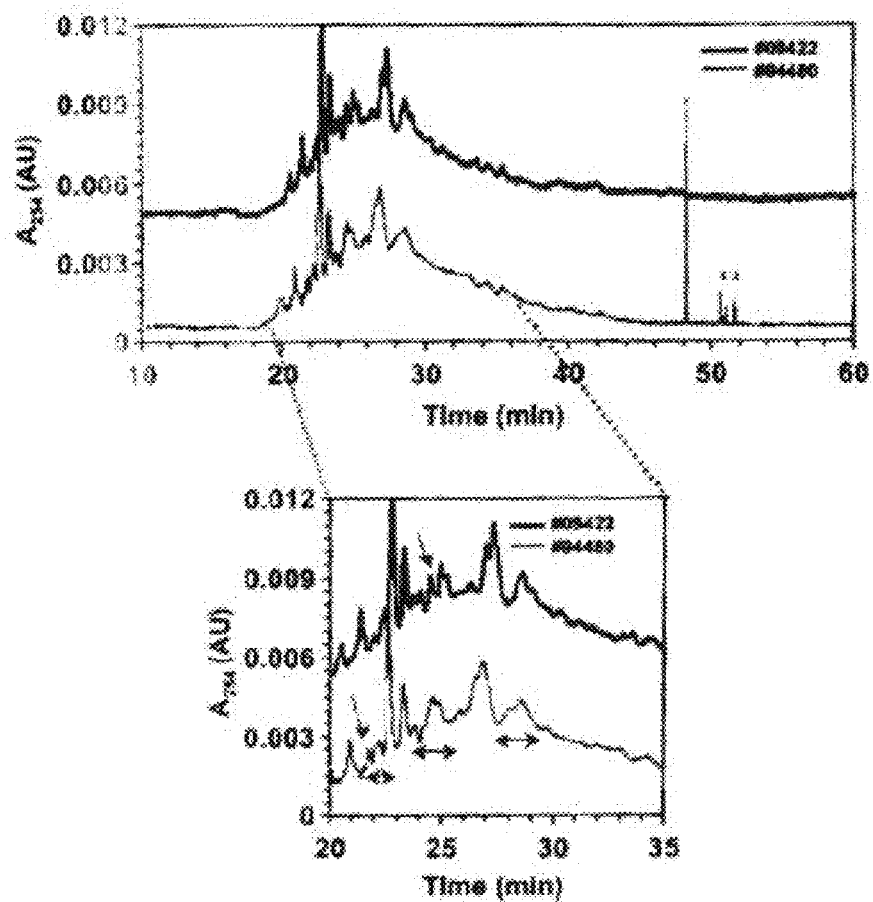
FIG. 12. Analysis of batch-to-batch variability of LMWHs. Two lots of AMAC-labeled Lovenox, No. 94480 and No. 09422, were resolved using 150 1M 4EP in 50 mM sodium phosphate buffer, pH 2.3, containing 10% DMSO. Note the difference in component pattern between the two lots in the 22, 25, and 27 min regions (marked in the bottom figure). Arrows at 22 and 25 min show new components present in the lot. In contrast, the component pattern is reversed for the region at 27 min. Peaks marked "x" are sudden disturbances due to bubble formation during the electrophoretic run.

A key aspect in the use of LMWHs as anticoagulants is the necessity to maintain consistency between different preparations. To assess whether our fingerprinting protocol can identify batch-to-batch variability, we studied two lots of enoxaparin, No. 94480 and No. 09422. Fingerprinting of both lots using 150 μM 4EP in 50 mM sodium phosphate buffer, pH 2.3, containing 10% DMSO showed a fairly consistent profile indicating that the two lots are essentially identical (FIG. 12). However, small differences in component pattern between the two lots are clearly noticeable. For example, the 22 and 25 min regions show new components, suggesting a discernible difference in composition, while the component pattern is reversed for the region at 27 mM (FIG. 12, expanded region). One can predict that this protocol can be expected to rapidly identify small and large compositional differences between lots, and thereby be especially useful in batch-to-batch analysis.

SUMMARY AND CONCLUSIONS

These results show that LMWHs can be readily fingerprinted using a simple capillary electrophoretic protocol. Without being bound by theory, it appears that the resolution in the presence of polyamines occurs because of recognition of the heparin fine structure resulting in the modification of overall charge density of the chains, which alters the electrophoretic mobility resulting in differential migration profiles. Our data show that the interaction of LMWH-polyamine is both structure and concentration dependent. Thus, the electrophoretic resolution appears to be a function of the affinity of the polyamine for heparin chains. The protocol uses readily available chemicals, is rapid, and is highly reproducible in producing distinctive fingerprint patterns.

The methods of the invention can be exploited, for example, for identifying intact LMWHs, for monitoring product quality, and for checking batch to batch variability. Although the resolution achieved using a single resolving agent is sufficient, the power of fingerprinting can be further expanded using a mixture of resolving agents. This is especially important considering that a number of LMWHs are being rapidly introduced in the world market.

Agent 5EH was found to be especially good at resolving enoxaparin and Sigma LMWH into several baseline-resolved peaks. It is likely that full baseline resolution will become possible with selected modifications to the protocol, e.g., the use of laser-induced fluorescence. This will enable detailed sequence analysis of nearly all LMWH chains through tandem CE-MS/MS approaches. A major advantage of the MS-based analysis is the possibility of identifying the proportion of LMWH chains containing the high-affinity pentasaccharide sequence, which governs anticoagulant activity in vivo [2]. Likewise, it is likely that the CE-MS/MS approach will become useful in deciphering heparin structure-activity relationships in areas other than coagulation.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

1. Cushman M, Tsai A W, White R H, Heckbert S R, Rosamond W D, Enright P, Folsom A R. Deep vein throm- 1. bosis and pulmonary embolism in two cohorts: the longitudinal investigation of thromboembolism etiology. Am J. Med. 2004; 117:19-25.
2. Desai U R. New antithrombin-based anticoagulants. Med Res Rev. 2004; 24:151-181.
3. Rabenstein D L. Heparin and heparan sulfate: structure and function. Nat Prod Rep. 2002; 19:312-331.
4. Capila I, Linhardt R J. Heparin-protein interactions. Angew Chem Int Ed Engl. 2002; 41:391-412.
5. Fareed J, Iqbal O, Nader H, Mousa S, Wahi R, Coyne E, Bick R L. Generic low molecular weight heparins: a significant dilemma. Clin Appl Thromb Hemost. 2005; 11: 363-366.
6. Fareed J, Leong W L, Hoppensteadt D A, Jeske W P, Walenga J, Wahi R, Bick R L. Generic low-molecular-weight heparins: some practical considerations. Semin Thromb Hemost. 2004; 30:703-713.
7. Turnbull J E, Gallagher J T. Oligosaccharide mapping of heparan sulphate by polyacrylamide-gradient-gel electrophoresis and electrotransfer to nylon membrane. Biochem J. 1988; 251:597-608.
8. Linhardt R J, Loganathan D, al-Hakim A, Wang H M, Walenga J M, Hoppensteadt D, Fareed J. Oligosaccharide mapping of low molecular weight heparins: structure and activity differences. J Med. Chem. 1990; 33:1639-1645.
9. Edens R E, al-Hakim A, Weiler J M, Rethwisch D G, Fareed J, Linhardt R J. Gradient polyacrylamide gel electrophoresis for determination of molecular weights of heparin preparations and low-molecular-weight heparin derivatives. J Pharm Sci. 1992; 81:823-827.
10. Rozenberg G I, Espada J, de Cidre L L, Eiján A M, Calvo J C, Bertolesi G E. Heparan sulfate, heparin, and heparinase activity detection on polyacrylamide gel electrophoresis using the fluorochrome tris(2,2'-bipyridine) ruthenium (II). Electrophoresis 2001; 22:3-11.
11. Malsch R, Harenberg J, Piazolo L, Huhle G, Heene D L. Chromatographic and electrophoretic applications for the analysis of heparin and dermatan sulfate. J Chromatogr B Biomed Appl. 1996; 685:223-231.
12. Kristensen H I, Tromborg E M, Nielsen J R, Nielsen J I, Johansen K B, Ostergaard P B. Development and validation of a size exclusion chromatography method for determination of molecular masses and molecular mass distribution in low molecular weight heparin. Thromb Res. 1991; 64:131-141.
13. Volpi N. Characterization of heparins with different relative molecular masses (from 11,600 to 1600) by various analytical techniques. J Chromatogr. 1993; 622:13-20.
14. Komatsu H, Yoshii K, Ishimitsu S, Okada S, Takahata T. Molecular mass determination of low-molecular-mass heparins. Application of wide collection angle measurements of light scattering using a high-performance gel permeation chromatographic system equipped with a low-angle laser light-scattering photometer. J Chromatogr. 1993; 644:17-24.
15. Komatsu H, Takahata T, Tanaka M, Ishimitsu S, Okada S. Determination of the molecular-weight distribution of low-molecular-weight heparins using high-performance gel permeation chromatography. Biol Pharm Bull. 1993; 16:1189-1193.
16. Malsch R, Harenberg J. High-performance size exclusion chromatography and polyacrylamide gel electrophoresis for characterization of unfractionated and low molecular mass glycosaminoglycans. Semin Thromb Hemost. 1994; 20:135-143.
17. Malsch R, Harenberg J, Guerrini M, Toni G, Casu B, Heene D L. Semisynthesis and analysis of lipophilically modified unfractionated and low molecular mass heparins. Semin Thromb Hemost. 1994; 20:182-192.
18. Desai U R, Linhardt R J. Molecular weight of low molecular weight heparins by 13C nuclear magnetic resonance spectroscopy. Carbohydr Res. 1994; 255:193-212.
19. Mulloy B, Gee C, Wheeler S F, Wait R, Gray E, Barrowcliffe T W. Molecular weight measurements of low molecular weight heparins by gel permeation chromatography. Thromb Haemost. 1997; 77:668-674.
20. Rice K G, Kim Y S, Grant A C, Merchant Z M, Linhardt R J. High-performance liquid chromatographic separation of heparin-derived oligosaccharides. Anal Biochem. 1985; 150:325-331.
21. Rosenfeld L, Prior M T, Girardi L M. Comparison of the separation of bovine heparin by strong anion exchange and by gel filtration chromatography. Thromb Res. 1991; 64:203-211.
22. Pervin A, Gallo C, Jandik K A, Han X J, Linhardt R J. Preparation and structural characterization of large heparin-derived oligosaccharides. Glycobiology. 1995; 5:83-95.
23. Hileman R E, Smith A E, Toida T, Linhardt R J. Preparation and structure of heparin lyase-derived heparan sulfate oligosaccharides. Glycobiology. 1997; 7:231-239.
24. Turnbull J E. Analytical and preparative strong anion-exchange HPLC of heparan sulfate and heparin saccharides. Methods Mol. Biol. 2001; 171:141-147.
25. Chuang W L, McAllister H, Rabenstein L. Chromatographic methods for product-profile analysis and isolation of oligosaccharides produced by heparinase-catalyzed depolymerization of heparin. J Chromatogr A. 2001; 932: 65-74.
26. Vivés R R, Goodger S, Pye D A. Combined strong anion-exchange HPLC and PAGE approach for the purification of heparan sulphate oligosaccharides. Biochem J. 2001; 354: 141-147.
27. Thanawiroon C, Linhardt R J. Separation of a complex mixture of heparin-derived oligosaccharides using reversed-phase high-performance liquid chromatography. J Chromatogr A. 2003; 1014:215-223.
28. Chai W, Luo J, Lim C K, Lawson A M. Characterization of heparin oligosaccharide mixtures as ammonium salts using electrospray mass spectrometry. Anal Chem. 1998; 70: 2060-2066.
29. Pope R M, Raska C S, Thorp S C, Liu J. Analysis of heparan sulfate oligosaccharides by nano-electrospray ionization mass spectrometry. Glycobiology. 2001; 11:505-513.
30. Kuberan B, Lech M, Zhang L, Wu Z L, Beeler D L, Rosenberg R D. Analysis of heparan sulfate oligosaccharides with ion pair-reverse phase capillary high performance liquid chromatography-microelectrospray ionization time-of-flight mass spectrometry. J Am Chem. Soc. 2002; 124:8707-8718.
31. Saad O M, Leary J A. Compositional analysis and quantification of heparin and heparan sulfate by electrospray ionization ion trap mass spectrometry. Anal Chem. 2003; 75:2985-2995.
32. Thanawiroon C, Rice K G, Toida T, Linhardt R J. Liquid chromatography/mass spectrometry sequencing approach for highly sulfated heparin-derived oligosaccharides. J Biol. Chem. 2004; 279:2608-2615.
33. Saad O M, Ebel H, Uchimura K, Rosen S D, Bertozzi C R, Leary J A. Compositional profiling of heparin/heparan sulfate using mass spectrometry: assay for specificity of a novel extracellular human endosulfatase. Glycobiology. 2005; 15:818-826.

34. Casu B, Guerrini M, Naggi A, Toni G, De-Ambrosi L, Boveri G, Gonella S, Cedro A, Ferró L, Lanzarotti E, Paterno M, Attolini M, Valle M G. Characterization of sulfation patterns of beef and pig mucosal heparins by nuclear magnetic resonance spectroscopy. Arzneimittelforschung. 1996; 46:472-477.
35. Guerrini M, Bisio A, Torn G. Combined quantitative (1)H and (13)C nuclear magnetic resonance spectroscopy for characterization of heparin preparations. Semin Thromb Hemost. 2001; 27:473-482.
36. Sudo M, Sato K, Chaidedgumjorn A, Toyoda H, Toida T, Imanari T. (1)H nuclear magnetic resonance spectroscopic analysis for determination of glucuronic and iduronic acids in dermatan sulfate, heparin, and heparan sulfate. Anal Biochem. 2001; 297:42-51.
37. Guerrini M, Guglieri S, Naggi A, Sasisekharan R, Torri G. Low molecular weight heparins: structural differentiation by bidimensional nuclear magnetic resonance spectroscopy. Semin Thromb Hemost. 2007; 33:478-487.
38. Desai U R, Linhardt R J. Molecular weight of heparin using 13C nuclear magnetic resonance spectroscopy. J Pharm Sci. 1995; 84:212-215.
39. Ampofo S A, Wang H M, Linhardt R J. Disaccharide compositional analysis of heparin and heparan sulfate using capillary zone electrophoresis. Anal Biochem. 1991; 199:249-255.
40. Desai U R, Wang H, Ampofo S A, Linhardt R J. Oligosaccharide composition of heparin and low-molecular-weight heparins by capillary electrophoresis. Anal Biochem. 1993; 213:120-127.
41. Pervin A, al-Hakim A, Linhardt R J. Separation of glycosaminoglycan-derived oligosaccharides by capillary electrophoresis using reverse polarity. Anal Biochem. 1994; 221:182-188.
42. Lamari F N, Militsopoulou M, Mitropoulou T N, Hjerpe A, Karamanos N K. Analysis of glycosaminoglycan-derived disaccharides in biologic samples by capillary electrophoresis and protocol for sequencing glycosaminoglycans. Biomed Chromatogr. 2002; 16:95-102.
43. Ruiz-Calero V, Moyano E, Puignou L, Galceran M T. Pressure-assisted capillary electrophoresis-electrospray ion trap mass spectrometry for the analysis of heparin depolymerised disaccharides. J Chromatogr A. 2001; 914: 277-291.
44. Damm J B, Overklift G T, Vermeulen B W, Fluitsma C F. and van Dedem G W. Separation of natural and synthetic heparin fragments by high-performance capillary electrophoresis. J Chomatogr. 1992; 608:297-309.
45. Duchemin V, le Potier I, Troubat C, Ferrier D. and Taverna M. Analysis of intact heparin by capillary electrophoresis using short end injection configuration. Biomed Chromatogr. 2002; 16:127-133.
46. Toida T, Linhardt R J. Detection of glycosaminoglycans as a copper (II) complex in capillary electrophoresis. Electrophoresis 1996; 17:341-346.
47. Stefansson M, Novotny M. Separation of complex oligosaccharide mixtures by capillary electrophoresis in the open-tubular format. Anal. Chem. 1994; 66:1134-1140.
48. Ramasamy I, Kennedy J, Tan K. Capillary electrophoresis for characterization of low molecular weight heparins. Lab Hematol. 2003; 9:64-66.
49. Patel R P, Narkowicz C, Hutchinson J P, Hilder E F, Jacobson G A. A simple capillary electrophoresis method for the rapid separation and determination of intact low molecular weight and unfractionated heparins. J Pharm Biomed Anal. 2008; 46:30-35.

We claim:
1. A method of characterizing or "fingerprinting" a sample of polydisperse heparins, comprising the steps of
forming a mixture comprising said polydisperse heparins and at least one polyamine resolving agent; and
analyzing said mixture using a technique that separates molecules based on a charge to mass ratio.
2. The method of claim 1, wherein said method is capillary electrophoresis.
3. The method of claim 1, wherein said polyamine has the general structure

Formula I

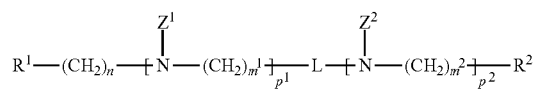

where
$R^1$=NHX, where X=H or a branched or unbranched lower alkyl (e.g. C1-C3); or $R^1$ is absent;
$R^2$=NHY, where Y=H or a branched or unbranched lower alkyl (e.g. C1-C3); or Y is absent;
$Z^1$ and $Z^2$=H or a branched or unbranched lower alkyl (e.g. C1-C3) and may be the same or different;
$m^1$ and $m^2$=0-6 and may be the same or different;
n=1-6;
$p^1$ and $p^2$=0-30, and may be the same or different, but may not both be 0; and where if $p^1$ or $p^2$>1, then values of $m^1$ and $m^2$ in different p groups that are present in said polyamine may be the same or different; and
L=absent; or
L=—$(CH_2)_q$—, where q=1-4; or
L=—C(O)—$(CH_2)_r$—C(O)—, where r=0-4; or
L=—C(O)—$C_6H_4$—C(O)—.
4. The method of claim 1, wherein L and p2 are absent, and the polyamine is selected from the group consisting of spermidine, triethylenetetramine, tetraethylenepentamine, spermine and pentaethylenehexamine.
5. The method of claim 4, wherein L, p2, R1 and Y are absent, and the polyamine is a cyclic polyamine selected from 1,4,7-triazacyclononane and 1,4,7,10-tetraazacyclododecane.
6. The method of claim 1, wherein said polydisperse heparins are low molecular weight heparins.
7. The method of claim 1, further comprising the step of labeling said polydisperse heparins with a detectable organic label.
8. The method of claim 3, wherein said at least one polyamine has the general structure

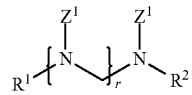

where r=1-30 and $Z^1$ may be the same or different in each instance.
9. The method of claim 3, wherein said at least one polyamine has the general structure

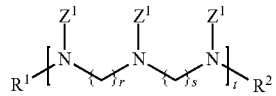

where r=1-30 and s=1-30 and t=1-30; r, s and t may be the same or different; and $Z^1$ may be the same or different in each instance.

10. The method of claim 3, wherein said at least one polyamine has the general structure

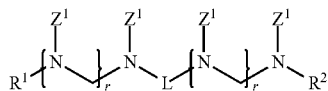

where r=1-30 and $Z^1$ may be the same or different in each instance.

11. The method of claim 3, wherein said at least one polyamine has the general structure

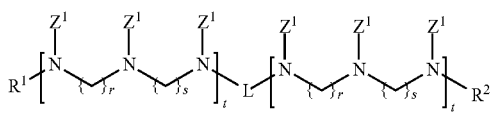

where r=1-30 and s=1-30 and t=1-30; r, s and t may be the same or different; and $Z^1$ may be the same or different in each instance.

12. The method of claim 3, wherein L is selected from

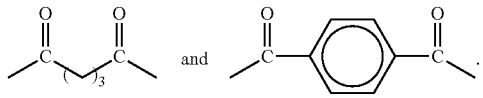

13. The method of claim 1, wherein said polydisperse heparins are suitable for clinical use.

14. A method of verifying the authenticity of an unknown sample of complex heparins, comprising the steps of
    forming a mixture comprising said unknown sample of complex heparins and a polyamine resolving agent,
    analyzing said mixture by a method that separates macromolecules according to a charge to mass ratio; then,
    based on results obtained in said analyzing step, determining a pattern of heparin migration for said unknown sample of complex heparins; and
    comparing said pattern of heparin migration for said unknown sample to a pattern of heparin migration for a known authentic heparin sample; and
        if said pattern of heparin migration for said unknown sample of complex heparins is the same as said pattern of heparin migration for said known authentic heparin sample, then concluding that said unknown sample of complex heparins is authentic; or
        if said pattern of heparin migration for said unknown sample of complex heparins differs from said pattern of heparin migration for said known authentic heparin sample, then concluding that said unknown sample of complex heparins is not authentic.

15. A method for enhancing resolution, based on a charge to mass ratio, of a mixture of polydisperse heparin molecules, comprising the step of adding a polyamine resolving agent to said mixture of polydisperse heparin molecules prior to performing a separation of said polydisperse heparin molecules based on a charge to mass ratio.

* * * * *